US007256606B2

(12) United States Patent
Wenzel et al.

(10) Patent No.: US 7,256,606 B2
(45) Date of Patent: Aug. 14, 2007

(54) METHOD FOR TESTING PIXELS FOR LCD TFT DISPLAYS

(75) Inventors: Axel Wenzel, Augsburg (DE); Ralf Schmid, Poing (DE); Matthias Brunner, Kirchheim (DE)

(73) Assignee: Applied Materials, Inc., Santa Clara, CA (US)

( * ) Notice: Subject to any disclaimer, the term of this patent is extended or adjusted under 35 U.S.C. 154(b) by 34 days.

(21) Appl. No.: 10/977,510

(22) Filed: Oct. 29, 2004

(65) Prior Publication Data

US 2006/0028230 A1 Feb. 9, 2006

Related U.S. Application Data

(60) Provisional application No. 60/598,667, filed on Aug. 3, 2004.

(51) Int. Cl.
*G01R 31/00* (2006.01)
*G01R 31/307* (2006.01)
(52) U.S. Cl. ........................................ 324/770; 324/751
(58) Field of Classification Search .................. None
See application file for complete search history.

(56) References Cited

U.S. PATENT DOCUMENTS

| | | | |
|---|---|---|---|
| 3,983,401 A | 9/1976 | Livesay |
| 4,362,945 A | 12/1982 | Riecke |
| 4,437,044 A | 3/1984 | Veith |
| 4,495,966 A | 1/1985 | Longamore |
| 4,528,452 A | 7/1985 | Livesay |
| 4,684,808 A | 8/1987 | Plies et al. |
| 4,725,736 A | 2/1988 | Crewe |
| 4,740,705 A | 4/1988 | Crewe |
| 4,760,567 A | 7/1988 | Crewe |
| 4,764,818 A | 8/1988 | Crewe |
| 4,819,038 A | 4/1989 | Alt |
| 4,843,312 A | 6/1989 | Hartman et al. |
| 4,862,075 A | 8/1989 | Choi et al. |
| 4,870,357 A | 9/1989 | Young et al. |
| 4,899,105 A | 2/1990 | Akiyama |
| 4,983,833 A | 1/1991 | Brunner et al. |

(Continued)

FOREIGN PATENT DOCUMENTS

EP    0 204 855    12/1986

(Continued)

OTHER PUBLICATIONS

Brunner—Development of Puma 5500/10K Platform, vol. 5, Jan. 2001, pp. 13-14.

(Continued)

*Primary Examiner*—Ernest Karlsen
(74) *Attorney, Agent, or Firm*—Patterson & Sheridan LLP (57) ABSTRACT

The present invention provides a method of electron beam testing of liquid crystal displays comprising non-uniform electrodes having a conductive portion and a dielectric portion. In accordance with methods of the present invention, the diameter of the electron beam is increased so that the beam is less focused, i.e., enlarged or "blurred," over a non-uniform electrode area. The diameter of the beam is increased so that the beam generates secondary electrons from the conductive portion of the non-uniform electrode area. The configured test beam may be circular, elliptical, or other suitable shapes.

21 Claims, 5 Drawing Sheets

U.S. PATENT DOCUMENTS

| | | | |
|---|---|---|---|
| 4,985,681 A | 1/1991 | Brunner et al. | |
| 5,124,635 A | 6/1992 | Henley | |
| 5,170,127 A | 12/1992 | Henley | |
| 5,175,495 A | 12/1992 | Brahme et al. | |
| 5,177,437 A | 1/1993 | Henley | |
| 5,258,706 A | 11/1993 | Brunner et al. | |
| 5,268,638 A | 12/1993 | Brunner et al. | |
| 5,278,494 A | 1/1994 | Obigane | |
| 5,285,150 A | 2/1994 | Henley et al. | |
| 5,369,359 A | 11/1994 | Schmitt | |
| 5,371,459 A | 12/1994 | Brunner et al. | |
| 5,414,374 A | 5/1995 | Brunner et al. | |
| 5,430,292 A | 7/1995 | Honjo et al. | |
| 5,504,438 A | 4/1996 | Henley | |
| 5,801,764 A | 9/1998 | Koizumi et al. | |
| 5,834,773 A | 11/1998 | Brunner et al. | |
| 5,892,224 A | 4/1999 | Nakasuji | |
| 5,973,323 A | 10/1999 | Adler et al. | |
| 5,982,190 A | 11/1999 | Toro-Lira | |
| 6,137,303 A | 10/2000 | Deckert et al. | |
| 6,559,454 B1 | 5/2003 | Murrell et al. | |
| 6,566,897 B2 | 5/2003 | Lo et al. | |
| 6,570,553 B2 | 5/2003 | Hashimoto et al. | |
| 6,630,975 B1 * | 10/2003 | Terashita | 349/139 |
| 6,730,906 B2 | 5/2004 | Brunner et al. | |
| 6,765,203 B1 | 7/2004 | Abel | |
| 6,777,675 B2 | 8/2004 | Parker et al. | |
| 6,828,587 B2 | 12/2004 | Yamazaki et al. | |
| 6,833,717 B1 | 12/2004 | Kurita et al. | |
| 2003/0218456 A1 | 11/2003 | Brunner et al. | |

FOREIGN PATENT DOCUMENTS

| | | |
|---|---|---|
| EP | 0 370 276 | 10/1989 |
| EP | 0 537 505 | 9/1992 |
| EP | 0 542 094 | 11/1994 |
| EP | 0 932 182 | 7/1999 |
| EP | 0 999 573 | 5/2000 |
| EP | 1 045 425 | 10/2000 |
| EP | 1 045 426 | 10/2000 |
| JP | 60039748 | 3/1985 |
| JP | 63088741 | 4/1988 |
| JP | 63088742 | 4/1988 |
| JP | 63166132 | 7/1988 |
| JP | 63318054 | 12/1988 |
| JP | 1 213944 | 8/1989 |
| JP | 1 307148 | 12/1989 |
| JP | 6167538 | 6/1994 |
| JP | 7302563 | 11/1995 |
| JP | 8173418 | 7/1996 |
| JP | 11 264940 | 9/1999 |
| JP | 2000 223057 | 8/2000 |
| JP | 2000 268764 | 9/2000 |
| JP | 2001 033408 | 2/2001 |
| JP | 2002 039976 | 2/2002 |
| JP | 2002 048740 | 2/2002 |
| JP | 2002 257997 | 9/2002 |
| JP | 2002 310959 | 10/2002 |
| JP | 2002 343294 | 11/2002 |
| JP | 2004 014402 | 1/2004 |
| WO | WO 92/09900 | 6/1992 |
| WO | WO 99/23684 | 5/1999 |

OTHER PUBLICATIONS

Brunner—TFT Array Testing: Replacing Mechanics by Electron Beam Deflection, vol. 6, Apr. 2001, pp. 15-17.

* cited by examiner

METHOD FOR TESTING PIXELS FOR LCD TFT DISPLAYS

CROSS-REFERENCE TO RELATED APPLICATIONS

This application claims priority to a U.S. Provisional Patent Application No. 60/598,667 filed on Aug. 3, 2004, which is entitled "Method for Testing Multi-Domain Vertical Alignment Pixels for TFT Displays," and is incorporated by reference herein in its entirety.

BACKGROUND OF THE INVENTION

1. Field of the Invention

The present invention relates to testing of pixels of a flat panel display. In particular, embodiments of the invention relate to the testing of pixels by directing an electron beam onto a non-uniform electrode area.

2. Description of the Related Art

In years past, a common display for computers and other electronic products has been the cathode ray tube, or CRT. The CRT served as the standard display for personal computers (PC's) and televisions during the last half of the twentieth century. The CRT generally operates on a curved glass panel to form a display.

Recently, active matrix liquid crystal displays, or LCD's, have been commercially developed. The LCD has several advantages over the CRT, including higher picture quality, lighter weight, lower voltage requirements, and low power consumption. LCD displays are beneficial for flat panel displays, and have been commercialized of late in many portable electronic devices such as calculator screens, personal digital assistant (PDA) screens, portable computer (notebook) screens, mobile telephone displays, and small computer and television screens. In addition, larger LCD displays are now being employed in flat-screen televisions for the consumer market.

One type of active matrix LCD comprises liquid crystal material sandwiched between a TFT-array substrate and a color filter substrate. The TFT-array substrate comprises an array of thin film transistors (TFT's) each coupled to a pixel electrode. The color filter substrate comprises different color filter portions and a common electrode. When a certain voltage is applied to a pixel electrode, an electric field is created between the pixel electrode and the common electrode, orienting the liquid crystal material to allow light to pass therethrough for that particular pixel.

Figure 1:
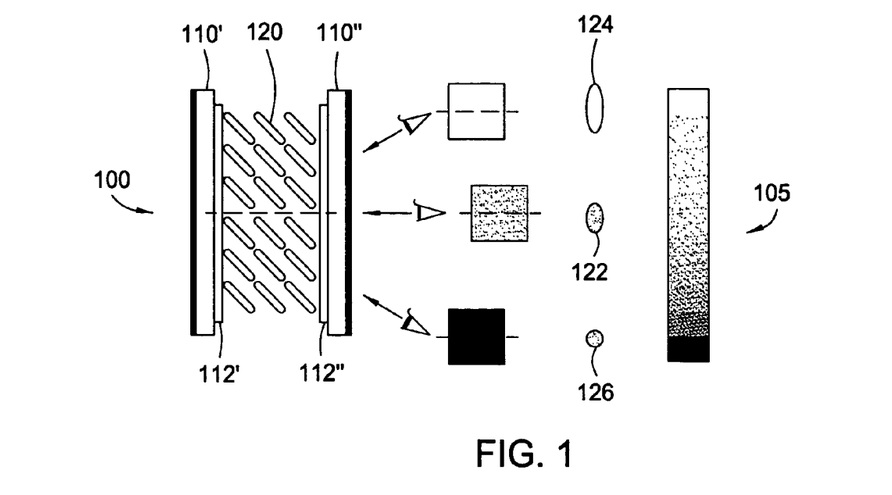
FIG. 1 is a schematic diagram showing one pixel of a liquid crystal display comprising a uniform pixel electrode.

FIG. 1 is a schematic diagram showing one pixel of a liquid crystal display 100 comprising a uniform pixel electrode. This diagram is taken from the web site of Fujitsu, found currently at http://www.fme.fujitsu.com/products/displays/lcdvatech.html. Liquid crystal material 120 is sandwiched between the TFT-array substrate 110' and the color filter substrate 110". Since the TFT-array substrate 110' comprises a uniform pixel electrode 112', the molecules of the liquid crystal orient in a single direction when a certain voltage is applied to the pixel electrode. The light intensity of the display 100 is dependent on the view direction in reference to the liquid crystal orientation. Thus, the TFT-LCD having a uniform pixel electrode has a drawback in that the effective viewing angle is narrow.

Figure 2:
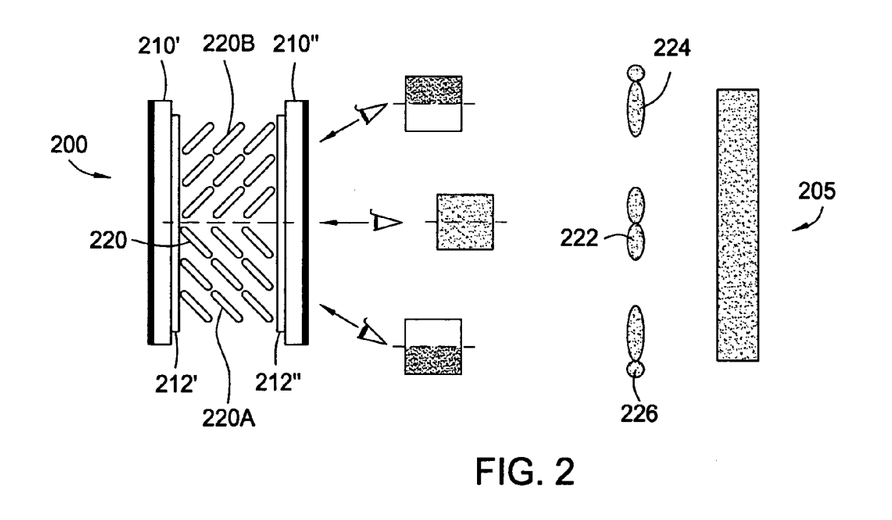
FIG. 2 is a schematic diagram showing one embodiment of one pixel of a liquid crystal display comprising a non-uniform electrode.

FIG. 2 is a schematic diagram showing one embodiment of one pixel of a liquid crystal display 200 comprising a non-uniform electrode. This diagram is taken from the web site of Fujitsu, found currently at http://www.fme.fujitsu.com/products/displays/lcdvatech.html. Liquid crystal material 220A and 220B is sandwiched between the TFT-array substrate 210' and the color filter substrate 210". The TFT-array substrate 210' comprises a non-uniform electrode 212'. The non-uniform electrode comprises dielectric lines formed over a conductive portion. The dielectric lines cause the liquid crystal material to orient in multiple directions. As a consequence, the display 200 seems bright when viewed at different angles by the viewer. This type of display having a non-uniform electrode comprising dielectric lines formed over a conductive portion is referred to as a multi-domain vertical alignment (MVA) display.

Figure 3:
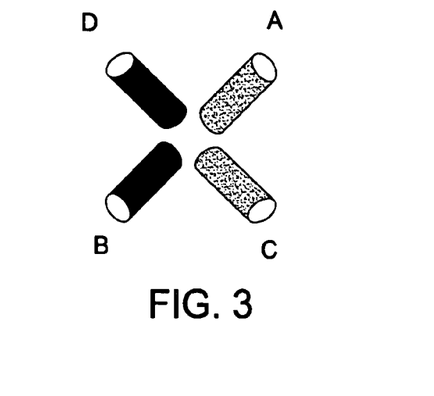
FIG. 3 and FIG. 4 are schematic diagrams of one example of a MVA display in which the liquid crystal can be oriented in four directions
Figure 4:
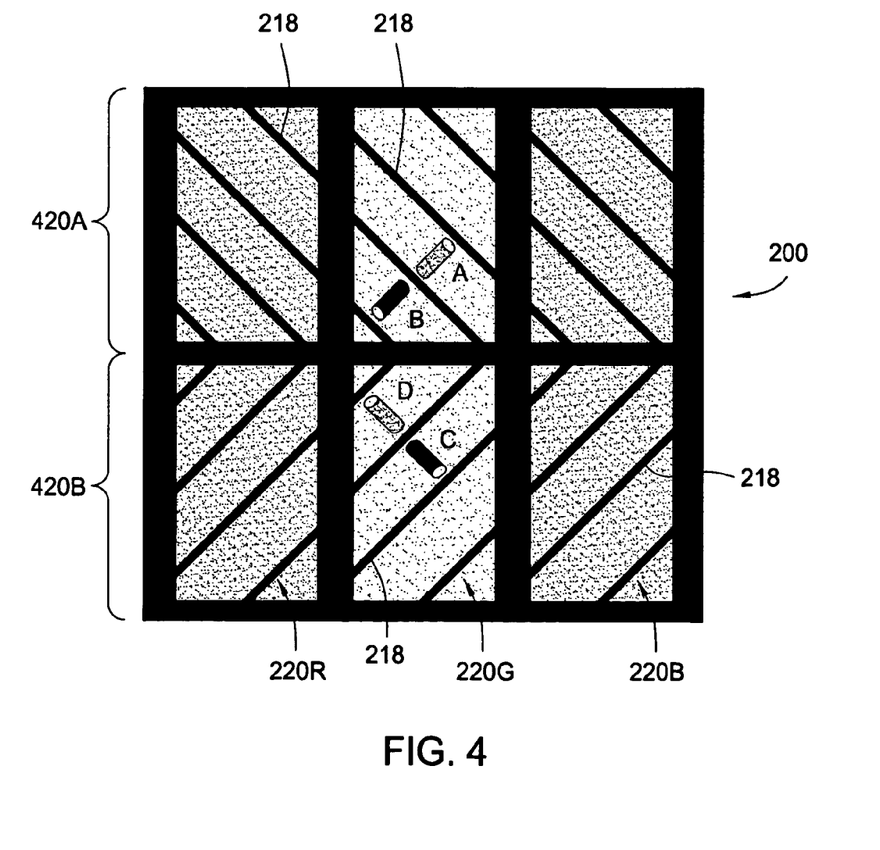

FIG. 3 and FIG. 4 are schematic diagrams of one example of a MVA display in which the liquid crystal can be oriented in four directions, designated as domains A, B, C, and D. In FIG. 4, six pixels can be seen having dielectric lines 218 formed over conductive portions 220B, G, and R. The dielectric lines 218 are used to divide and align the liquid crystal in a pixel into a plurality of alignment orientations.

Another type of display having a non-uniform electrode is referred to as an In Plane Switching (IPS) display. The display comprises a pair of electrodes formed over the TFT-array substrate. In one arrangement, the IPS display employs a pair of electrodes shaped as interlocking fingers. The liquid crystal molecules remain parallel to the substrates. As a consequence, the viewing angle of the display is increased.

As sizes increase for MVA-type and IPS-type displays, manufacturers must add more pixels and transistors to the substrate. Those of ordinary skill in the art appreciate that even moderately-sized color displays may employ transistors that number in the millions. If there is a problem with any of the transistors, it creates a defective pixel on the display. As the number of transistors increases, the likelihood that a bad transistor might be created within a display also increases. Therefore, manufacturers of large LCD's will test all or a percentage of pixels in a display as part of quality control.

Electron beam testing (EBT) can be used to monitor and troubleshoot defects during the manufacturing process. In a typical EBT process, TFT response within the pixels is monitored to provide defect information. For example, in EBT testing, certain voltages are applied to the thin film transistors, and the electron beam is directed to the individual pixel electrodes under investigation. Secondary electrons emitted from the pixel electrode area are sensed to determine the TFT voltages.

During testing, an electron beam is positioned over each pixel electrode of the TFT array, one after the other. To accomplish this movement, a substrate is first positioned on a table below an electron beam column. A substrate area (sometimes referred to as a sub-display area) may be moved under the electron beam column. Once a sub-display area of a substrate area is under the beam column, the beam is moved sequentially over each pixel electrode within the substrate area. After this area has been tested, the table is moved for testing of the next area. In some newer systems, two to four beams are utilized in parallel to simultaneously test separate substrate areas.

Electron beam testing of displays comprising non-uniform electrodes is problematic due to the conductive portions and dielectric portions of the non-uniform electrode. As a consequence, an improved method of testing displays comprising non-uniform electrodes is needed.

SUMMARY OF THE INVENTION

The present invention provides a method of electron beam testing of liquid crystal display comprising non-uniform electrodes having a conductive portion and a dielectric portion. In accordance with methods of the present invention, the diameter of the electron beam is increased so that the beam is less focused, i.e., enlarged or "blurred," over a non-uniform electrode area. The diameter of the beam is increased so that the beam generates secondary electrons from the conductive portion of the non-uniform electrode area. The configured test beam may be circular, elliptical, or other suitable shapes.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 5:
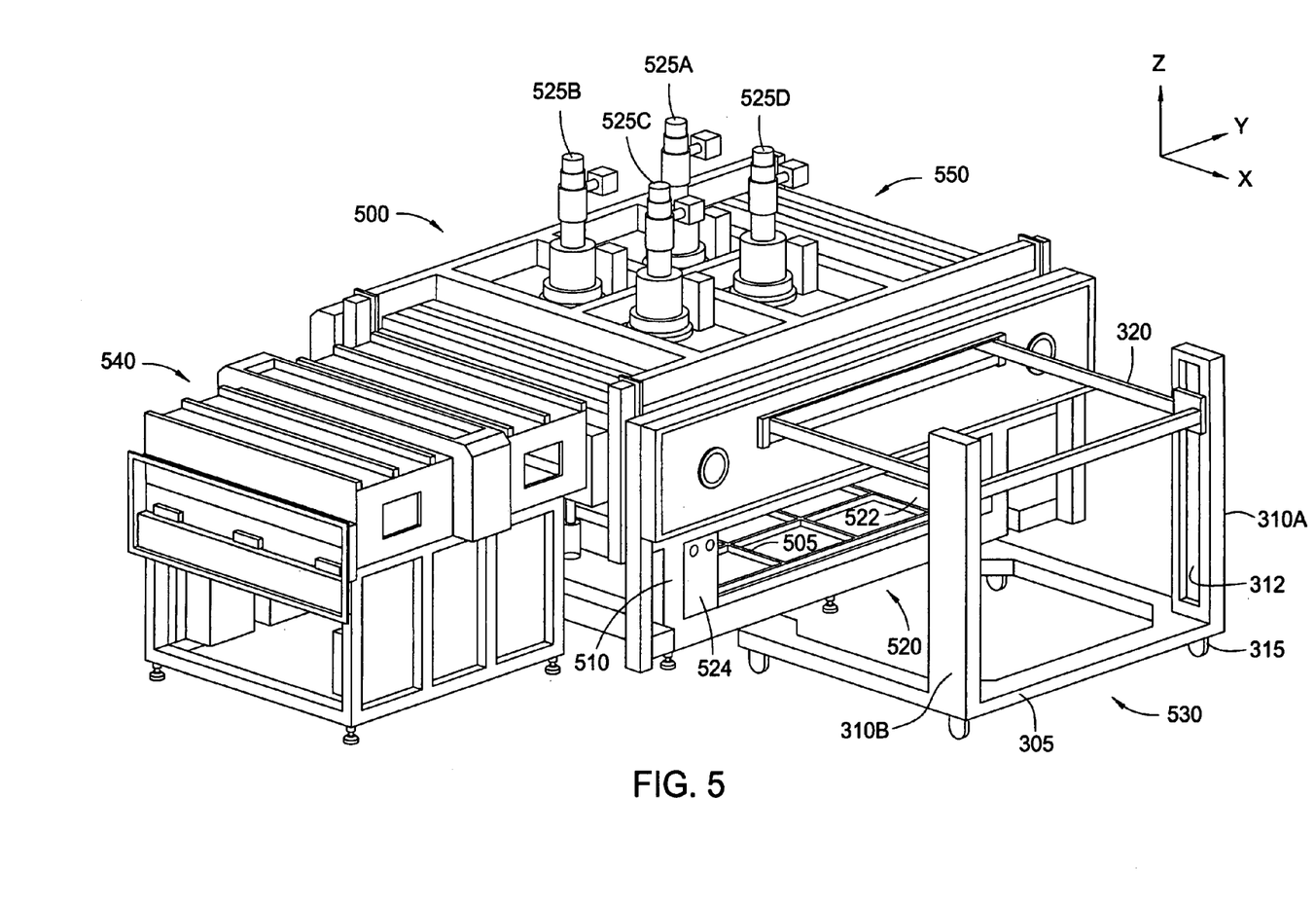
FIG. 5 is a schematic perspective view of an exemplary electron beam test (EBT) system.

FIG. 5 is a schematic perspective view of an exemplary electron beam test (EBT) system 500. The illustrated EBT system 500 is capable of testing large panel substrates, up to and exceeding 1.9 meters by 2.2 meters. The EBT system 500 is for purposes of illustration, it being understood that any EBT system of any size may be modified to practice the methods disclosed here.

The electron beam test system 500 generally includes a prober storage assembly 520, a prober transfer assembly 530, a load lock chamber 540, and a testing chamber 550. The prober storage assembly 520 houses one or more probers 505 proximal the test chamber 550 for easy use and retrieval. Preferably, the prober storage assembly 520 is disposed beneath the test chamber 550 as shown in FIG. 1, reducing the clean room space needed for a contaminant free and efficient operation. The prober storage assembly 520 preferably has dimensions approximating those of the testing chamber 550 and is disposed on a mainframe 510 supporting the testing chamber 550. The prober storage assembly 520 includes a shelf 522 disposed about the mainframe 510 to provide a support for the one or more probers 505. The prober storage assembly 520 may further include a retractable door 524 that can seal off the storage area and protect the stored probers 505 when not in use.

The prober transfer assembly 530 is a modular unit disposable near the testing chamber 550 for transferring a prober 505 between the prober storage assembly 520 and the test chamber 550. The prober transfer assembly 530 includes a base 305 connected to two or more vertical support members 310A, 310B (two are shown). Wheels or casters 315 may be arranged on a bottom surface of the base 305 to easily maneuver the assembly 530 when desired.

The prober transfer assembly 530 further includes a lift arm 320 that is attached at one end thereof to the support members 310A, 310B. The support members 310A, 310B each include a recessed track 312 (one is shown in this view) for mating engagement with the lift arm 320. One or both of the recessed tracks 312 may house a linear actuator, a pneumatic cylinder, a hydraulic cylinder, a magnetic drive, a stepper or servo motor, or other type of motion device (not shown). The recessed tracks 312, working in conjunction with the motion device (not shown), guide and facilitate the vertical movement of the lift arm 320. The lift arm 320 is configured to be inserted into the test chamber 550 or within the storage assembly 520 to retrieve and deliver the prober 505.

The load lock chamber 540 is disposed adjacent and connected to the testing chamber 550. These chambers 540, 550 share a common environment which is typically maintained at vacuum conditions by a pump (not shown) coupled through the testing chamber 550. The load lock chamber 540 transfers substrates between the testing chamber 550 and the outside which is typically a clean room at atmospheric pressure. The load lock chamber 540 may function as an isolated processing environment that is capable of being heated or cooled as well as pressurized or de-pressurized, depending on system requirements. Consequently, load lock chamber 540 enables the transfer of substrates into and out of the testing chamber 550 without exposure to outside contaminants.

Four EBT columns 525 A, B, C, D are shown in FIG. 5. The EBT columns 525A/B/C/D are disposed on an upper surface of the test chamber 550. When actuated, the columns deliver a beam of electrons onto the electrodes on the substrate in order to excite the electrodes during testing.

Additional details concerning the testing of pixels and the operation and features of the illustrative EBT test system 500 are disclosed in U.S. Pat. No. 6,833,717, filed Feb. 12, 2004 and issued on Dec. 21, 2004. That patent is entitled "Electron Beam Test System with Integrated Substrate Transfer Module," and is incorporated herein in its entirety by reference.

During testing, a substrate is positioned on a table below the beam and the beam is moved to sequentially test the electrodes of the TFT array. It has been observed that during EBT testing of an MVA-type display, the insulator lines formed on the TFT-array substrate interfere with the electron responses. For example, in reference to FIG. 4, during EBT testing of an MVA-type display, it is desired that the electron beam excite electrons on the exposed conductive portions 220 B/G/R between the dielectric lines 218. However, a beam may be unintentionally directed primarily on one of the insulator lines 218 rather than a conductive portion, thereby interfering with the electron responses from the conductive area. Similarly, it has been observed that the conductive line fingers structure of an IPS display interferes with the electron responses. For example, a beam may find itself directed primarily on a dielectric portion formed between the pair of electrodes, thereby interfering with the electron responses. In either instance, the secondary electron signal detected when a beam is positioned solely on the dielectric portion is different than when the beam is positioned on the conductive portion.

It is desirable to avoid a situation where different electron signal values are generated depending on the position of the electron beam within a non-uniform electrode area. Therefore, the methods of the present invention employ an enlarged or "defocused" test beam that essentially generates an average or blended signal. Stated another way, increasing the diameter of the test beam allows the signal interference of the dielectric portion to be substantially reduced.

Figure 6:
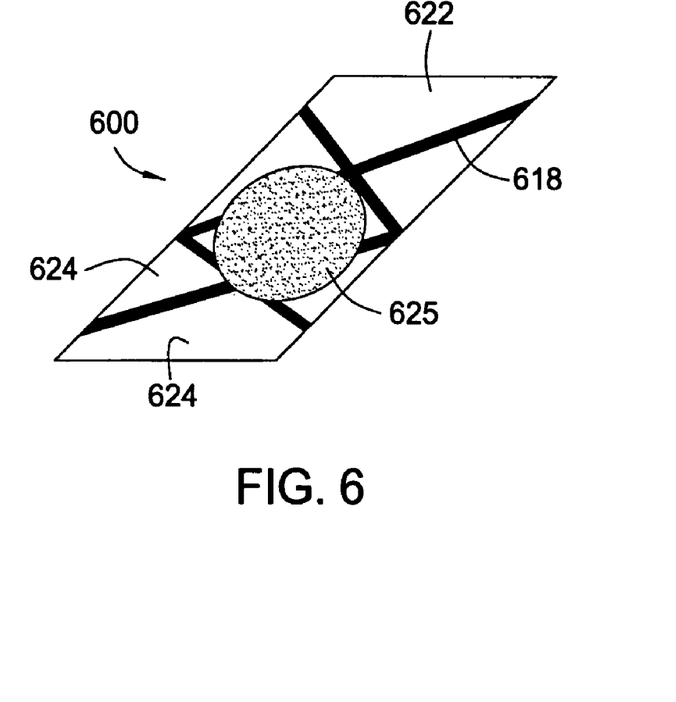
FIG. 6 is a schematic perspective view of one embodiment of a non-uniform electrode area

FIG. 6 is a schematic perspective view of one embodiment of a non-uniform electrode area 600. The non-uniform electrode area 600 is intended to represent a single pixel in an MVA-type display. The dielectric lines 618 are formed over a conductive portion 622 and 624. In the illustrative non-uniform electrode 600, conductive portion 624 is exposed between the insulating lines 618.

To overcome the problem of inconsistent electron beam response for the MVA-type display, the electron beam diameter is increased, or "blurred," between two times and ten times (or more) than the width of the dielectric lines 618. In one aspect, the electron beam diameter is increased between about four times and eight times more than the width of the dielectric lines 618. In one non-limiting example, the width of the dielectric lines 618 may be about 10 μm. In this instance, the electron beam diameter is increased to between about 20 μm and about 100 μm. Increasing the diameter of the electron beam causes less proportional charging of the dielectric lines 618, and essentially averages out the effect of the dielectric lines 618 on electrode excitement.

An electron beam 625 is shown in FIG. 6 being directed over a portion of the non-uniform electrode 600 during testing. Here, the electron beam 625 is generally circular in shape. The beam 625 has a diameter that is significantly greater than a width of the various dielectric lines 618.

Figure 7:
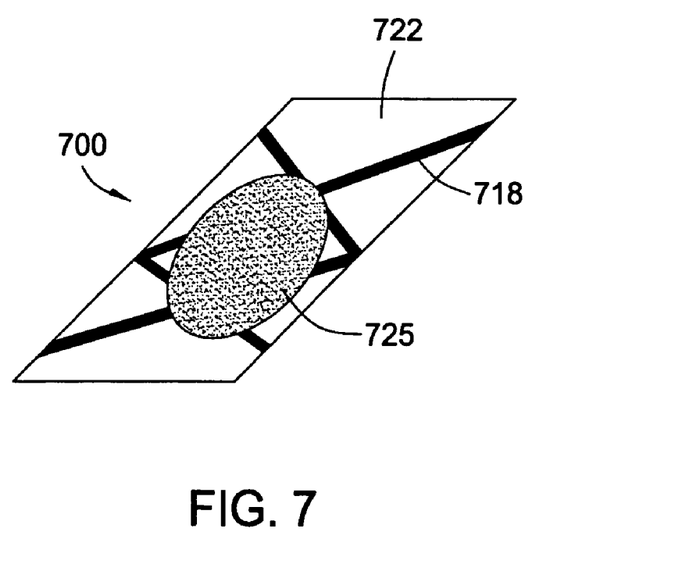
FIG. 7 is a schematic perspective view of another embodiment of a non-uniform electrode area.

Other beam configurations may be employed. FIG. 7 is a schematic perspective view of another embodiment of a non-uniform electrode area 700. Here, the electron beam 725 is generally elliptical in shape. The diameter of the beam 725 is measured across its minor axis.

Figure 8:
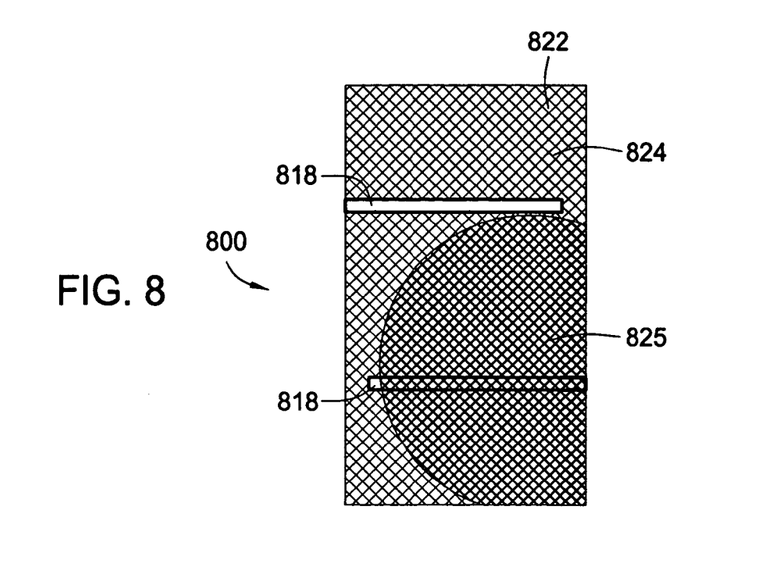
FIG. 8 is a schematic plan view of a still another non-uniform electrode area.

The size of the "blurred" beam may also be measured in comparison to the area of the pixel electrode area itself. In one embodiment of the methods herein, the area of the beam is increased to have a size that is at least about 50% of the non-uniform electrode area being tested. FIG. 8 is a schematic plan view of a still another non-uniform electrode area 800. Two adjacent lines 818 are shown over the non-uniform electrode area 800. The pixel area is intended to be generic such that the lines 818 may be either dielectric or conductive, and the adjacent areas between the lines 818 are either conductive or dielectric respectively. It can be seen in FIG. 8 that an electron test beam 825 is being directed onto the non-uniform electrode area 800. The beam 825 is covering portions of both a line 818 and an area adjacent the line 818. The beam 825 has a diameter that is sufficient to generate secondary electrons from a conductive portion. Moreover, the beam is of sufficient diameter so that the electron signal will be substantially the same when the beam 825 is moved to a different non-uniform electrode within the same TFT array.

In the view of FIG. 8, the beam area is at least 50% of the entire non-uniform electrode area. In one embodiment, the area of the beam 825 could be as large as the distance from line 818 to an adjacent line 818. In one aspect, the electron beam has an area that is between about 50% and 90% of the non-uniform electrode area 800 under investigation.

Figure 9:
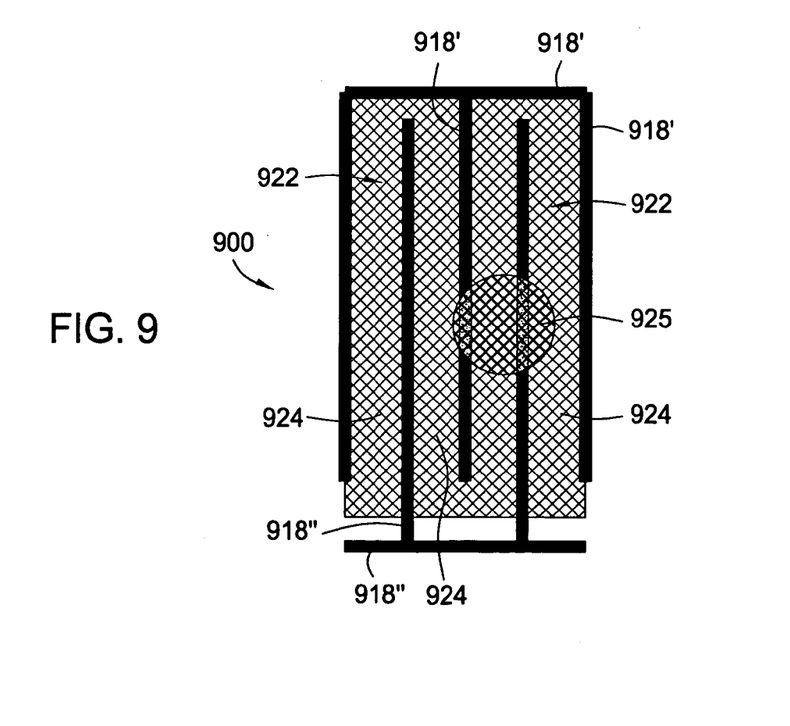
FIG. 9 is a schematic plan view of yet another non-uniform electrode area.

FIG. 9 is a schematic plan view of yet another non-uniform electrode area 900, such as an IPS-type cell. The non-uniform electrode area 900 comprises a pair of electrodes 918', 918" forming an interlacing finger structure. A width is defined between the electrodes 918', 918" with the width traversing an dielectric portion 924.

An electron test beam 925 is being directed onto the non-uniform electrode area 900. The beam 925 is at least covering portions of the electrode 918', the electrode 918", and a dielectric portion 924 between the electrodes 918', 918". The beam is of sufficient diameter so that the electron signal will be substantially the same when the beam 925 is moved to a different non-uniform electrode within the same TFT array.

The diameter of electron beam 925 is increased, or "blurred," between two times and ten times (or more) than the diameter of the width of one of the electrodes 918', 918". In one aspect, the electron beam diameter is increased between about four times and eight times more than the width of one of the electrodes 918', 918". Increasing the diameter of the electron beam causes less proportional charging of the dielectric portion 924, and essentially averages out the effect of the dielectric portion 924 on electrode excitement.

In another embodiment of the methods described herein, a focused beam is used to first scan over a positioning/alignment mark on the substrate. Since the display substrate position under the beam is typically shifted by substrate loading errors, table positioning errors, and other errors, and since the beam positioning control has an error margin, scanning over a positioning/alignment mark on the substrate helps to eliminate these positional errors and correct the beam position in reference to the substrate. For example, the beam may be focused to an area about 20% or less than the area of the non-uniform electrode, then, the electron beam is scanned over the positioning/alignment mark. Then, the beam may be defocused by altering the current in the focusing lens and/or altering the current in a magnetic focusing coil. The electron beam may be defocused to an area greater than about 20% than the area of the non-uniform electrode or to other sizes as disclosed herein. Then, the defocused beam is directed sequentially over the targeted non-uniformed electrode area of the TFT-array.

The inventions herein have been described primarily with reference to MVA-type and IPS-type displays. However, it is understood that the present inventions are not limited to these types of devices, and that these devices are described merely for purposes of illustration. In this respect, the methods described herein have utility in testing devices of any other type where the display has non=uniform electrodes.

While the foregoing is directed to embodiments of the present invention, other and further embodiments of the invention may be devised without departing from the basic scope thereof, and the scope thereof is determined by the claims that follow.

The invention claimed is:

1. A method for conducting electron beam testing of TFT devices on a flat panel display substrate comprising non-uniform electrode areas, each non-uniform electrode area having a conductive portion and a dielectric portion, the method comprising:

generating an enlarged electron test beam having an area that is sufficient to cover at least partially the dielectric portion and at least partially the conductive portion; and directing the enlarged electron test beam onto the non-uniform electrode area, wherein the area of the enlarged electron test beam is at least about 50% of the non-uniform electrode area.

2. The method of claim 1, wherein the area of the enlarged electron test beam is between about 50% and about 90% of the non-uniform electrode area.

3. The method of claim 1, wherein the enlarged electron test beam is circular in shape.

4. The method of claim 1, wherein the enlarged electron test beam is elliptical in shape.

5. The method of claim 1, wherein the enlarged electron test beam is oval in shape.

6. A method for conducting electron beam testing of TFT devices on a flat panel display substrate comprising non-uniform electrode areas, each non-uniform electrode area having dielectric lines formed over a conductive portion, the method comprising:

generating an electron test beam having an increased area including a diameter that is sufficient to cover at least partially one of the dielectric lines and to cover at least partially the conductive portion; and directing the electron test beam onto the non-uniform electrode areas of the flat panel display substrate, wherein the diameter of the electron beam is between about two times and about ten times a width of one of the dielectric lines.

7. The method of claim 6, wherein the diameter of the electron beam is between about four times and about eight times a width of one of the dielectric lines.

8. The method of claim 6, wherein the electron test beam is circular in shape.

9. The method of claim 6, wherein the electron test beam is elliptical in shape and the diameter of the configured electron test beam is measured across a minor axis.

10. The method of claim 6, wherein the flat panel display substrate comprises a multi-domain vertical alignment (MVA) display substrate.

11. The method of claim 6, wherein the electron test beam is oval in shape.

12. A method for conducting electron beam testing of TFT devices on a flat panel display substrate comprising non-uniform electrodes areas, each non-uniform electrode area comprising a first electrode and a second electrode separated by a dielectric portion, the method comprising:

generating an enlarged electron test beam to have an area having a diameter that is sufficient to cover at least partially the first electrode, at least partially the second electrode, and at least partially the dielectric portion; and directing the enlarged electron test beam onto the non-uniform electrode areas of the flat panel display substrate, wherein the diameter of the enlarged electron beam is between about two times and about ten times a width of one of the dielectric lines.

13. The method of claim 12, wherein the diameter of the enlarged electron beam is between about four times and about eight times a width of one of the dielectric lines.

14. The method of claim 12, wherein the enlarged electron test beam is circular in shape.

15. The method of claim 12, wherein the enlarged electron test beam is elliptical in shape and the diameter of the enlarged electron test beam is measured across a minor axis.

16. The method of claim 12, wherein the flat panel display substrate comprises an in plane switching display substrate.

17. The method of claim 12, wherein the enlarged electron test beam is oval in shape.

18. A method for conducting electron beam testing of TFT devices on a flat panel display substrate comprising non-uniform electrodes areas, each non-uniform electrode area comprising a first electrode and a second electrode separated by a dielectric portion, the method comprising:

directing an electron test beam onto the flat panel display substrate;

blurring the electron test beam to have an area having a diameter that is sufficient to cover at least partially the first electrode, at least partially the second electrode, and at least partially the dielectric portion; and directing the electron test beam onto the non-uniform electrode areas of the flat panel display substrate, wherein the diameter of the electron beam is between about two times and about ten times a width of one of the dielectric lines.

19. The method of claim 18, wherein the electron test beam is oval in shape.

20. The method of claim 18, wherein the electron test beam is circular in shape.

21. The method of claim 18, wherein the electron test beam is elliptical in shape and the diameter of the electron test beam is measured across a minor axis.

* * * * *